(12) United States Patent
Cedarbaum

(10) Patent No.: US 8,748,496 B2
(45) Date of Patent: Jun. 10, 2014

(54) METHODS OF TREATMENT OF HYPERURICEMIA AND ASSOCIATED DISEASE STATES

(75) Inventor: Jesse M. Cedarbaum, San Francisco, CA (US)

(73) Assignee: Elan Pharmaceuticals, Inc., South San Francisco, CA (US)

( * ) Notice: Subject to any disclaimer, the term of this patent is extended or adjusted under 35 U.S.C. 154(b) by 670 days.

(21) Appl. No.: 12/560,113

(22) Filed: Sep. 15, 2009

(65) Prior Publication Data

US 2010/0152305 A1    Jun. 17, 2010

Related U.S. Application Data

(60) Provisional application No. 61/097,023, filed on Sep. 15, 2008.

(51) Int. Cl.
*A61K 31/047* (2006.01)

(52) U.S. Cl.
USPC ........................................................ 514/729

(58) Field of Classification Search
CPC . A61K 31/047; A61K 2300/00; A61K 31/66; A61K 31/045; A61K 31/7004; A61K 31/22; A61K 45/06; A61K 31/185; A61K 31/525; A61K 31/56; A61K 31/70; A61K 38/465; A61K 31/075; A61K 31/16; A61K 51/00
See application file for complete search history.

(56) References Cited

U.S. PATENT DOCUMENTS

2008/0200437 A1 *   8/2008   Lehn et al. ................ 514/103

FOREIGN PATENT DOCUMENTS

WO    WO 98/57620 A2    12/1998
WO    WO 2006/053428 A1    5/2006

OTHER PUBLICATIONS

Schultz, C., Bioorganic Medicinal Chemistry, (Mar. 20, 2003), 11(6), pp. 885-898.*
The management of hyperuricemia and gout in patients with heart failure. The European Journal of Heart Failure (2002) vol. 4, pp. 403-410.*
International Search Report dated Nov. 27, 2009, PCT/US2009/056985.

* cited by examiner

*Primary Examiner* — Melenie McCormick
*Assistant Examiner* — Taina D Matos Negron
(74) *Attorney, Agent, or Firm* — Millen, White, Zelano & Branigan, PC

(57) ABSTRACT

The present disclosure relates to compositions and methods for reducing uric acid levels in a individual in need thereof. The present disclosure further relates to the treatment of hyperuricemia and diseases associated with high uric acid levels in mammals using scyllo-inositol.

19 Claims, 2 Drawing Sheets

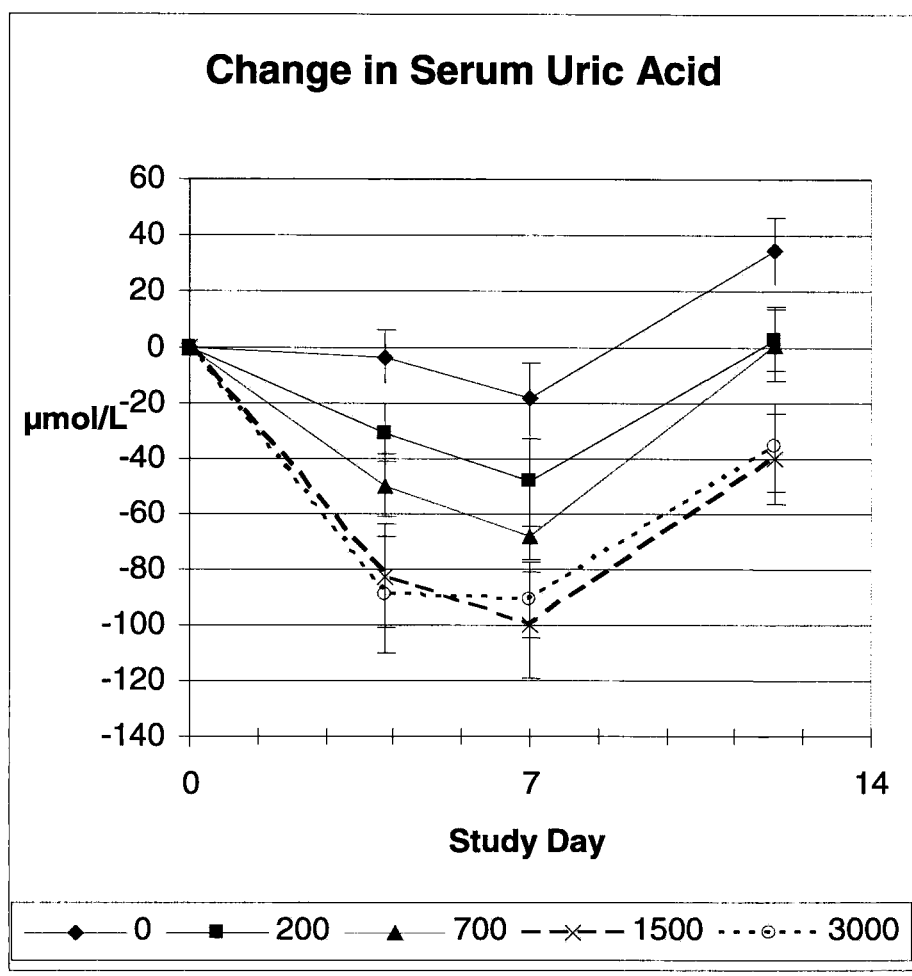

METHODS OF TREATMENT OF HYPERURICEMIA AND ASSOCIATED DISEASE STATES

This application claims the benefit of U.S. Provisional Application No. 61/097,023, filed Sep. 15, 2008, the disclosure of which is incorporated herein by reference in its entirety.

Uric acid (7,9-dihydro-1H-purine-2,6,8(3H)-trione; UA) has been implicated as a risk factor for several diseases or disease states. Kutzing, M. K. et al., JPET Vol. 324, No. 1, 1-7 (2008) (doi:10.1124/jpet.107.129031).

Abnormally high UA levels (i.e., hyperuricemic levels) in the blood contribute to a number of disease states, for example, gout, renal disease (Johnson, R. J., et al., Hypertension. 2003 June; 41(6):1183-90), atheroscleropathy (Hayden, M. R., Nutr Metab (Lond). 2004 Oct. 19; 1(1):10), cardiovascular disease (Hayden 2004; Alderman, M., Curr Med Res Opin. 2004 March; 20(3):369-79), metabolic syndrome (Hayden, 2004; Lin, J. D., Metabolism, 2007 June; 56(6): 751-6), urate lithiasis (Shekarriz B. et al., J. Urol., 2002 October; 168(4 Pt 1):1307-14) and hypertension (Johnson 2003). Although the art is not entirely settled on whether hyperuricemia is a cause or effect of some of those disease states mentioned above, there is mounting opinion and evidence that UA is a risk factor in these diseases, rather than the presence of UA as a biological marker (i.e., indicator) consequent to the disease state.

A number of studies demonstrate a link between hyperuricemia and gout (see for example, Lin, K. C. et al., J. Rheumatol., 2000; 27:1501-1505; Choi, H. K. et al., Ann Intern Med., 2005; 143:499-516), an inflammatory arthritis that results from the crystallization of UA within the joints (Choi et al., 2005). Further, studies report a direct positive association between serum urate levels and a future risk for gout. Specifically, as urate concentration increases, the risk for crystal formation increases, raising a patient's susceptibility to the development of gout (Lin et al., 2000).

It is generally accepted that gout and urate lithiasis are linked to hyperuricemia among other risk factors. Some studies have linked primary gout and urate lithiasis. (Pak, C. Y. et al., Kidney Int., 2001 August; 60(2):757-61).

Hyperuricemia, for men, can be a UA concentration greater than 386 µM (which is micromoles per liter or micromolar) in serum in one study (Klemp P. et al., Ann Rheum Dis. 56:22-26 (1997)) and greater than 420 µM in a separate study (Johnson, R. J. et al., Hypertension 41:1183-1190 (2003)). For women, most studies define hyperuricemia as a concentration greater than approximately 360 µM (Klemp 1997 and Johnson 2003). The normal range of UA concentrations falls somewhere between about 120 µM and about 380 µM, varying slightly depending on gender (Kutzing 2008). In some instances uric acid concentration in blood or serum is expressed in milligrams per deciliter (mg/dL); to convert a uric acid value from micromoles per liter to mg/dL, divide the value by 59.48.

After modification of diet, alcohol intake, and exercise levels for afflicted individuals, currently favored treatments for hyperuricemia include two types of drugs: xanthine oxidase inhibitors and uricosuric drugs. For example, those are presently the treatments of choice for gout. Xanthine oxidase inhibitors such as allopurinol, inhibit the production of UA by blocking the final two steps of urate synthesis. As a result, there is an increase in the pool of urate precursors, xanthine and hypoxanthine. Xanthine oxidase inhibitors are primarily used in patients who have an increased urate production compared to the norm.

Alternatively, if elevated UA concentrations are secondary to low urate clearance, uricosuric drugs, such as probenecid, sulfinpyrazone, and benzpromarone are used to reduce the serum UA concentration through the inhibition of a renal transporter that reabsorbs UA from the tubules which results in an increase in UA excretion (Emmerson, 1996; Choi et al., 2005). However, treatment of gout with uricosuric drugs can lead to uric acid nephrolithiasis (kidney stones). Another older, less used treatment for gout is administration of colchicine. Side effects have been reported for those existing treatments, and there is still an unmet need for safe and effective treatments for hyperuricemia and for diseases associated with hyperuricemia.

Scyllo-inositol has been found to lower uric acid levels in patients, and it has been found that scyllo-inositol lowers the amount of uric acid in the blood in a dose dependent manner. Therefore, scyllo-inositol can be useful in lowering uric acid levels in tissues or organs, blood, serum, urine, or combinations thereof and can have utility in treating conditions associated with aberrant levels of uric acid, such as conditions characterized by elevated levels of uric acid. Conditions associated with aberrant levels of uric acid may involve overproduction of uric acid, low excretion of uric acid, tumor lysis, a blood disorder, or a combination thereof.

Scyllo-inositol has utility in lowering abnormally high levels of uric acid in the blood (hyperuricemia) and has utility in treating diseases associated with hyperuricemia or having hyperuricemia as a risk factor, or in diseases, which are exacerbated by the presence of hyperuricemia. Such diseases include, but are not limited to, gout, atheroscleropathy, arterioloscleropathy, renal disease, cardiovascular disease, metabolic syndrome, urate lithiasis, and hypertension.

The present disclosure relates to a method of decreasing uric acid levels in a patient in need thereof in one or more tissues or organs, blood, serum, urine, or combinations thereof comprising administering to the patient an effective amount of scyllo-inositol to decrease the uric acid level in the patient compared to the patient's uric acid level before administration.

The present disclosure also relates a method of treating a patient suffering from a condition associated with aberrant levels of uric acid comprising administering to the patient an effective amount of scyllo-inositol to decrease the uric acid level in the patient compared to the patient's uric acid level before administration. In at least one embodiment, the condition is chosen from gout; a recurrent gout attack; gouty tophus; gouty arthritis; gouty nephropathy; eclampsia; atheroscleropathy; arterioloscleropathy; metabolic syndrome; diseases that involve accelerated formation and destruction of blood cells; hyperuricaemia; chronic hyperuricemia of polycythermia vera, of myeloid metaplasia, or of blood dyscrasia; hypertension; cardiovascular disease; coronary heart disease; Lesch-Nyhan or Kelley-Seegmiller syndrome to the extent of renal and/or gout-like symptoms; renal disease; kidney stones; renal failure; acute renal failure; joint inflammation; arthritis; urolithiasis; urate lithiasis; plumbism; hyperparathyroidism; psoriasis; and sarcoidosis.

The present disclosure further relates to a method of treating a condition associated with aberrant levels of uric acid in an individual at increased risk of developing the condition comprising administering to the individual a therapeutically effective amount of scyllo-inositol.

The present disclosure relates to a method of reducing serum uric acid levels in an individual in need thereof by administering a serum uric acid level lowering amount of scyllo-inositol. In another embodiment of the present disclosure, the individual to be treated has serum uric acid levels before treatment equal to or greater than 7 mg/dL (420 μmol/L). At least one condition treated using a method of the present disclosure is gout or any condition brought about by high levels of uric acid in the joints or kidneys or a serum uric acid level over 9 mg/dL (530 μmol/L).

In another embodiment, the present disclosure relates to a method of reducing the formation of tophi/tophus in an individual comprising administering to the individual a therapeutically effective amount of scyllo-inositol.

The present disclosure relates to a method for treating hyperuricemia in a patient in need thereof comprising administering to the patient an effective amount of scyllo-inositol to decrease the uric acid level in the patient compared to the patient's uric acid level before administration.

In another embodiment of the present disclosure, the amount of scyllo-inositol administered to the hyperuricemic patient ranges from about 150 mg/day to 7000 mg/day, from about 150 mg/day to 6000 mg/day, from about 200 mg/day to 6000 mg/day, from 400 mg/day to 6000 mg/day, from 150 mg/day to about 4000 mg/day, and further for example, from 200 mg/day to 3000 mg/day.

In another embodiment, the scyllo-inositol is administered to a patient, in a unit dosage form. In another embodiment, the unit dosage form is chosen from an immediate release dosage form and an extended release dosage form. In another embodiment of the present disclosure the unit dosage form comprises 150 mg, 250 mg, 500 mg, 750 mg, 800 mg, 1000 mg, or 2000 mg of scyllo-inositol.

In another embodiment of the present disclosure, a method of treating gout in a patient in need thereof comprising administering to the patient an effective amount of scyllo-inositol to decrease the uric acid level in the patient compared to the patient's uric acid level before administration. In another embodiment, the present disclosure relates to a method of treating gout, wherein the amount of scyllo-inositol administered to the patient ranges from about 150 mg/day to about 7000 mg/day, from about 150 mg/day to about 6000 mg/day, and such as, from about 150 mg/day to about 4000 mg/day. In another embodiment, scyllo-inositol is administered to the patient in the treatment of gout in a unit dosage form. In another embodiment, the unit dosage form is chosen from an immediate release dosage form and an extended release dosage form. In an aspect of the present disclosure, the unit dosage form comprising 150 mg, 250 mg, 500 mg, 750 mg, 800 mg, or 1000 mg of scyllo-inositol.

Another embodiment of the present disclosure relates to a method of treating a disease state having hyperuricemia as a risk factor in a patient in need thereof comprising administering to the patient an effective amount of scyllo-inositol to decrease the uric acid level in the patient compared to the patient's uric acid level before administration. In another embodiment, the disease state is chosen from atheroscleropathy, arterioloscleropathy, renal disease, cardiovascular disease, metabolic syndrome, urate lithiasis, and hypertension. In another embodiment, the amount of scyllo-inositol administered ranges from about 150 mg/day to about 7000 mg/day and further for example, from about 150 mg/day to about 6000 mg/day. In another embodiment in the method of treatment of the disease states, scyllo-inositol is administered in a unit dosage form. In another embodiment, the unit dosage form is chosen from an immediate release dosage form and an extended release dosage form. In another embodiment in the method of treatment of the disease states, the unit dosage form comprises 150 mg, 250 mg, 500 mg, 750 mg, 800 mg, 1000 mg, or 2000 mg of scyllo-inositol.

The present disclosure also relates to a method of treating a condition associated with aberrant levels of uric acid in an individual comprising determining the individual's average serum uric acid level and administering to the individual scyllo-inositol according to a regimen effective to maintain the individual's serum uric acid level at or below 5 mg/dL or 6 mg/dL. The average serum uric acid level is generally the average of two or more uric acid readings obtained from the individual. The readings may be taken within hours, days, or weeks of each other. In at least one embodiment of the present disclosure, the two or more readings are obtained at least a week apart.

A method of the present disclosure may also comprise administering in combination with scyllo-inositol, a second treatment, such as a second therapeutic agent, effective for the treatment of a condition associated with aberrant levels of uric acid, such as a disease mediated in part by hyperuricemia. Therefore, the present disclosure relates to a combination treatment for a condition associated with aberrant levels of uric acid comprising administering to the patient an effective amount of scyllo-inositol to decrease the uric acid level in the patient compared to the patient's uric acid level before administration and a second therapeutic agent. In at least one embodiment of the present disclosure, the second therapeutic agent is a uric acid lowering agent, such as a xanthine oxidase inhibitor. Therefore, the present disclosure also relates to a method for decreasing uric acid production, increasing uric acid excretion, or both comprising administering therapeutically effective amounts of scyllo-inositol and a uric acid lowering agent. Examples of uric acid lowering agents include, but are not limited to, allopurinol, febuxostat, 4-(5-pyridin-4-yl-1/f-[1,2,4]triazol-3-yl)pyridine-2-carbonitrile (FYX-051), or combinations thereof.

The present disclosure also relates to a pharmaceutical composition comprising an amount of scyllo-inositol effective to lower a mammal's uric acid level in blood compared to a baseline level and at least one pharmaceutical component chosen from a carrier, an excipient, and a vehicle. In additional embodiments, the pharmaceutical compositions are useful for treating gout. In additional embodiments, the pharmaceutical compositions are useful for reducing hypertension or cardiovascular events. In additional embodiments, the pharmaceutical composition is in unit dosage forms suitable for single administration of precise dosages. In additional embodiments, the amount of scyllo-inositol present in the unit dosage form ranges from about 150 mg to 2000 mg, such as from 150 mg to 1500 mg, such as from 100 mg to 2000 mg, such as from 100 mg to 1500 mg, or such as from 100 mg to 1000 mg. In additional embodiments, scyllo-inositol is administered in a single dose, once daily. In additional embodiments, scyllo-inositol is administered twice daily. In further or additional embodiments, scyllo-inositol is administered three times per day. In additional embodiments, scyllo-inositol is administered four times per day.

A pharmaceutical composition of the present disclosure may also comprise a second therapeutic agent, such as a uric acid lowering agent. Combinations of a scyllo-inositol and a second therapeutic agent, such as a uric acid lowering agent, in compositions of the present disclosure may be selected to provide additive effects or greater than additive effects, for example, synergistic effects. In an embodiment, the present disclosure relates to a pharmaceutical composition comprising a scyllo-inositol and a second therapeutic agent, such as a uric acid lowering agent, in combination with at least one pharmaceutically acceptable component chosen from a carrier, an excipient, and a vehicle, wherein the amounts of scyllo-inositol and second therapeutic agent are selected to provide an additive or synergistic effect in treating a condition disclosed herein, as a combined preparation for simultaneous, separate, or sequential use in treatment of a condition associated with aberrant levels of uric acids. In another embodiment, the present disclosure relates to a pharmaceutical composition comprising scyllo-inositol and a second therapeutic agent in combination with at least one pharmaceutically acceptable component chosen from a carrier, an excipient, and a vehicle, wherein the scyllo-inositol and second therapeutic agent are selected to provide a synergistic effect, as a combined preparation for simultaneous, separate, or sequential use in treatment of a condition associated with aberrant levels of uric acids. In another embodiment, the present disclosure relates to a pharmaceutical composition comprising scyllo-inositol and a second therapeutic agent, wherein said composition achieves a synergistic effect for treating a disease state in which hyperuricemia is a risk factor in a mammal in need thereof. The present disclosure also relates to a pharmaceutical composition in separate containers and intended for simultaneous or sequential administration to a subject especially to provide beneficial effects, comprising a scyllo-inositol and a second therapeutic agent, such as a uric acid lowering agent, both optionally together with pharmaceutically acceptable carriers, excipients, or vehicles.

The present disclosure relates to the use of scyllo-inositol in the preparation of a medicament for decreasing uric acid levels in one or more tissues or organs, blood, serum, urine, or combinations thereof. The present disclosure also relates to the use of scyllo-inositol in the preparation of a medicament for decreasing uric acid production, increasing uric acid excretion, or both. The present disclosure further relates to the use of scyllo-inositol in the preparation of a medicament for treating a condition associated with aberrant levels of uric acid. The present disclosure still further relates to the use of scyllo-inositol in the preparation of a medicament for treating a condition chosen from gout; a recurrent gout attack; gouty tophus; gouty arthritis; gouty nephropathy; eclampsia; artheroscleropathy; arterioloscleropathy; metabolic syndrome; diseases that involve accelerated formation and destruction of blood cells; hyperuricaemia; chronic hyperuricemia of polycythermia vera, of myeloid metaplasia, or of blood dyscrasia; hypertension; cardiovascular disease; coronary heart disease; Lesch-Nyhan syndrome or Kelley-Seegmiller syndrome to the extent of renal and/or gout-like symptoms; renal disease; kidney stones; renal failure; acute renal failure; joint inflammation; arthritis; urolithiasis; urate lithiasis; metabolic syndrome; plumbism; hyperparathyroidism; psoriasis; and sarcoidosis.

The present disclosure also relates to the use of a scyllo-inositol and at least one second therapeutic agent, composition, or combination treatment of the present disclosure for ameliorating disease severity, disease symptoms, and/or periodicity of recurrence of a condition disclosed herein. Further, the present disclosure relates to the use of a scyllo-inositol and a second therapeutic agent as a medicament. The medicament may be suitable for use in treating a condition disclosed herein or is suitable for use in patients who are at risk of developing a condition disclosed herein.

The present disclosure is further directed to a kit comprising a first container comprising a pharmaceutical composition comprising an amount of scyllo-inositol effective to lower a mammal's uric acid level in blood compared to a baseline level and at least one pharmaceutically acceptable component chosen from a carrier, an excipient, and a vehicle. The kit further comprises a second container comprising a second therapeutic agent.

BRIEF DESCRIPTION OF THE DRAWINGS

FIG. 2 shows the change in serum uric acid levels in subjects in the same study as summarized in FIG. 1.

DESCRIPTION

Figure 1:
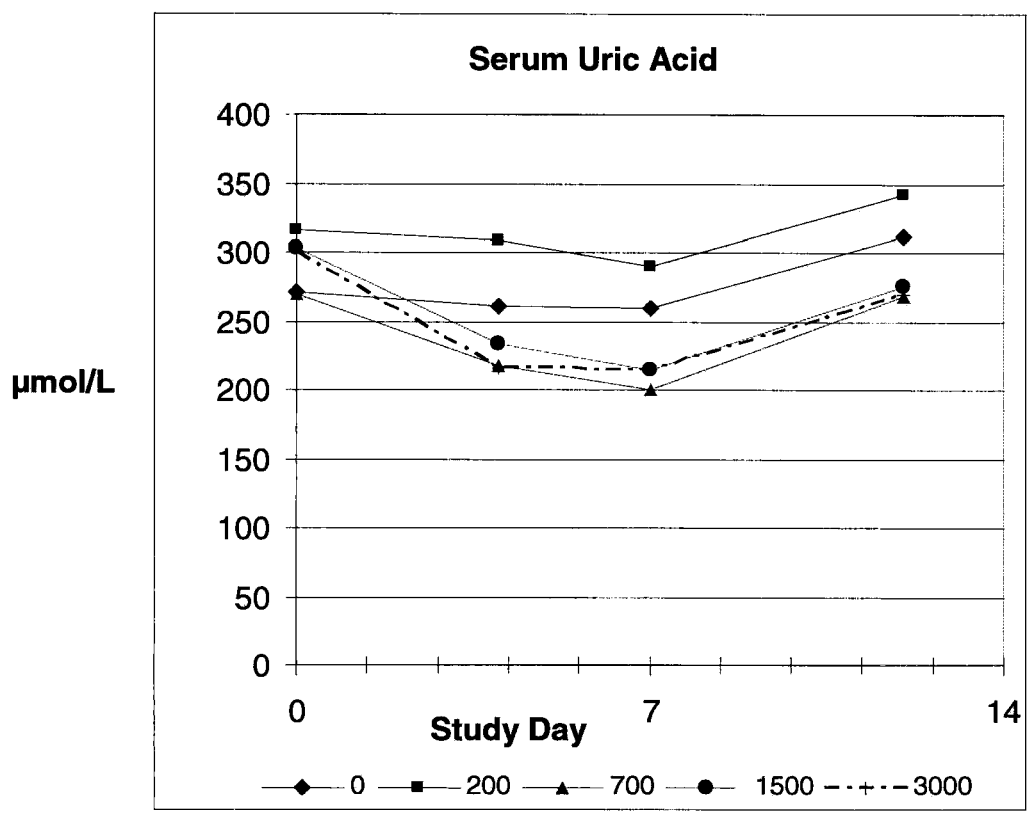
FIG. 1 shows a plot of serum levels of UA vs. time under administration of different dosages of scyllo-inositol to healthy human subjects. The legend shows doses that were 0 mg (control), 200 mg, 700 mg, 1500 mg, and 3000 mg per day. Measurements were taken at days 0 (baseline), 4, 7, and 12.

Particular aspects of the disclosure are described in greater detail below. The terms and definitions as used in the present application and as clarified herein are intended to represent the meaning within the present disclosure. The patent and scientific literature referred to herein and referenced above are hereby incorporated by reference. The terms and definitions provided herein control, if in conflict with terms and/or definitions incorporated by reference. Unless defined otherwise, all technical and scientific terms used herein have the same meaning as commonly understood by one of ordinary skill in the art.

Numerical ranges recited herein by endpoints include all numbers and fractions subsumed within that range (for example, from 1 to 5 includes 1, 1.5, 2, 2.75, 3, 3.90, 4, and 5). It is also to be understood that all numbers and fractions thereof are presumed to be modified by the term "about." The term "about" means plus or minus 0.1 to 50%, 5-50%, or 10-40%, such as 10-20%, such as 10% or 15%, of the number to which reference is being made. Further, it is to be understood that "a," "an," and "the" include plural referents unless the content clearly dictates otherwise. Aspects of the present disclosure requiring a particular value in a subject are substantially supported herein by population data in which the relevant value is assessed to be a meaningful delimitation of the subject population.

The phrase "a condition(s) associated with aberrant levels of uric acid" may be characterized by elevated levels of uric acid in at least one tissue or organ, blood, serum, urine, or combinations thereof. Generally, uric acid (UA) concentrations normally range from about 120 µM to about 380 µM (e.g., from about 2 mgd/L to about 7 or 8 mg/dL), varying slightly depending on gender. Elevated levels of UA may, for example, be greater than 5, 6, 7, or 8 mg/dL. The aberrant levels may result from overproduction of uric acid, low excretion of uric acid, tumor lysis, a blood disorder, or a combination thereof. Examples of conditions associated with aberrant levels of uric acid include, without limitation, those chosen from gout; a recurrent gout attack; gouty tophus; gouty arthritis; gouty nephropathy; eclampsia; artheroscleropathy; arterioloscleropathy, metabolic syndrome; diseases that involve accelerated formation and destruction of blood cells; hyperuricaemia; drug related hyperuricemia; chronic hyperuricemia of polycythemia vera, of myeloid metaplasia, or of blood dyscrasia; hypertension; cardiovascular disease; coronary heart disease; Lesch-Nyhan or Kelley-Seegmiller syndrome to the extent of renal and/or gout-like symptoms; renal disease; kidney stones; renal failure; acute renal failure; joint inflammation; arthritis; urolithiasis; urate lithiasis; plumbism; hyperparathyroidism; psoriasis; hypoxanthine-guanine phosphoribosyl transferase (HPRT) deficiency; and sarcoidosis.

In at least one embodiment, the condition is chosen from gout; a recurrent gout attack; gouty arthritis; gouty nephritis; eclampsia; or chronic hyperuricemia of polycythermia vera, of myeloid metaplasia, and of blood dyscrasia.

In an embodiment, the condition is a drug related hyperuricaemia where the drug may be one or more of nucleic acid metabolic antagonists, hypotensive diuretics, anti-tuberculosis drugs, anti-inflammatory analgesic drugs, hyperlipidemic drugs, therapeutic drugs for asthma, immunosuppressants, cytotoxic drugs, salicylic acid, pyrazinamide, ethambutol, nicotinic acid, ethanol, cyclosporine, or the like.

In other embodiments of the present disclosure, the condition is a disease state having hyperuricemia as a risk factor. A risk factor is a characteristic that has been implicated or demonstrated to be associated with (although not necessarily the direct cause of) a particular disease or syndrome. Risk factors can be used for targeting treatment efforts of individuals who may be particularly in danger of the disease or syndrome based on having a particular risk factor or combination of risk factors. Disease states in which hyperuricemia is a risk factor include without limitation atheroscleropathy, arterioloscleropathy, renal disease, cardiovascular disease, metabolic syndrome, urate lithiasis, and hypertension. It will be recognized by those of skill in the art that renal disease, atheroscleropathy, arterioloscleropathy, cardiovascular disease, metabolic syndrome, and hypertension are complex disease states in which there are more than one risk factor and an array of pathological processes. Treatment of those disease states by administration of scyllo-inositol is intended to treat that portion of the disease state that is associated with or affected by hyperuricemia.

In at least one embodiment of the present disclosure, the condition is gout and related symptoms.

In another embodiment of the present disclosure, the condition is hypoxanthine-guanine phosphoribosyltransferase (HPRT) deficiency caused by genetic mutations.

In another embodiment of the present disclosure, the condition is hypertension or edema.

In another embodiment of the present disclosure, the condition is acute renal failure.

The term "treating" refers to reversing, alleviating, or inhibiting the progress of a condition, or one or more symptoms of such condition, to which such term applies. The term also refers to maintaining the condition and/or symptom as-is such that the condition and/or symptom does not progress in severity. A treatment may be either performed in an acute or chronic way. The term also refers to reducing the severity of a condition or symptoms associated with such condition prior to affliction with the disease. Such reduction of the severity of a condition prior to affliction refers to administration of scyllo-inositol, or composition, or combination of the present disclosure to a subject that is not at the time of administration afflicted with the condition. The terms "treatment" and "therapeutically," refer to the act of treating, as "treating" is defined above. The purpose of intervention is to combat the condition and includes the administration of an active compound to delay the onset of the symptoms or complications, or alleviating the symptoms or complications, or eliminating the condition. For example, a compound, composition, or combination disclosed herein may be used to ameliorate symptoms associated with elevated levels of uric acid such as muscle spasm, localized swelling, inflammation, joint pains, muscle fatigue, stress feelings, or myocardial infarction.

The term "administering" or "administration" refers to the process by which scyllo-inositol, compositions, and/or combinations disclosed herein are delivered to a subject for treatment or prophylactic purposes. Scyllo-inositol, compositions, and/or combinations are administered in accordance with good medical practices taking into account the subject's clinical condition, the site and method of administration, dosage, subject age, sex, body weight, and other factors known to the physician. For example, the terms "administering" or "administration" as used herein refer to (1) providing, giving, dosing and/or prescribing by either a health practitioner or his authorized agent or under his direction scyllo-inositol, and (2) putting into, taking or consuming by the patient or person himself or herself, scyllo-inositol.

A "combination treatment," "administering in combination" or "administered in combination" means use of multiple pharmaceutical agents in combination as active ingredients administered concurrently to a patient being treated. The terms include use as a combination drug, use as a kit, and use in a combination characterized by independent administration of each by the same or different administration routes and the like. When administered in combination each component may be administered at the same time, or sequentially in any order at different points in time. Therefore, each component may be administered separately, but sufficiently close in time to provide a desired effect, such as an additive or synergistic effect. The first compound may be administered in a regimen that additionally comprises treatment with a second therapeutic agent. In embodiments of the present disclosure, the terms refer to the administration of scyllo-inositol and a second agent including separate administration of medicaments each containing one of the compounds, as well as simultaneous administration whether or not the compounds are combined in one formulation or whether they are in separate formulations.

An "additive effect" of a scyllo-inositol and a second therapeutic agent refers to an effect that is equal to the sum of the effects of the two individual agents.

A "synergistic effect" of a scyllo-inositol and a second therapeutic agent refers to an effect that is greater than the additive effect that results from the sum of the effects of the two individual agents.

A "uric acid lowering agent" refers to an agent effective in reducing uric acid levels in tissues or organs, blood, serum, urine, or combinations thereof and refers to an agent known to reduce blood or serum uric acid levels. Uric acid lowering agents, include without limitation, NSAIDs, colchicine, cinchophan, bucolome, corticosteroids, adenocorticotropic hormones (ACTH), sulfinpyrazone, Arcalyst™ (rilonacept), XOMA 052, xanthine oxidoreductase inhibitors such as 4-(5-pyridin-4-yl-1/f-[1,2,4]-triazol-3-yl)pyridine-2-carbonitrile (FYX-051), xanthine oxidase inhibitors such as allopurinol, tisopurine, hydroxyakalone, TEI-6720, febuxostat (Adenuric™, Uloric®), and Y-700; uricosurics such as benziodarone, benzbromarone, probenecid and RDEA594; supplements of the uricase protein, an inhibitor of the organic anion transport channels and/or voltage sensitive transport channels acting in the kidney, including but not limited to losartan, benzbromaraone, benziodarone, probenicid, sulfinpyrazone ethebencid, orotic acid, ticrynafen and zoxazolamine; a supplement of the uricase protein which may be delivered as a conjugate with polyethylene glycol or another delivery system, a urate channel inhibitor, uricase derivatives such as Rasburicase and Pegylated uricase; gene based therapies such as uricase overexpression or blockade of URAT-1, or combinations thereof.

The terms "subject," "individual," and "patient" refer to an animal including a warm-blooded animal, such as a mammal. Mammal includes without limitation any members of the kingdom Mammalia. Mammal includes humans, but the term also includes domestic animals bred for food or as pets, such as horses, cows, sheep, poultry, fish, pigs, cats, dogs, and zoo animals, goats, apes (e.g., gorilla or chimpanzee), and rodents such as rats and mice. Subjects for treatment include mammals, such as humans, susceptible to (e.g., being pre-disposed), suffering from, or that have suffered from a condition disclosed herein.

The phrase "at least one pharmaceutically acceptable component chosen from a carrier, an excipient, and a vehicle" refers to a medium which is useful for preparing a pharmaceutical composition that is generally safe, non-toxic and neither biologically nor otherwise undesirable. It is generally selected so that it does not interfere with the effectiveness or activity of an active ingredient and is not toxic to the hosts to which it is administered. The phrase as used in the specification and claims include both one and more than one such carrier, excipient, or vehicle. Acceptable carriers, excipients, or vehicles may be chosen from any of those commercially used in the art. By way of example, a carrier, excipient, or vehicle includes, but not limited to, diluents, binders, adhesives, lubricants, disintegrates, bulking agents, wetting or emulsifying agents, pH buffering agents, and miscellaneous materials such as absorbants that may be needed in order to prepare a particular composition. Examples of carriers, excipients, and vehicles include, but are not limited to, saline, buffered saline, dextrose, water, glycerol, ethanol, and combinations thereof. The use of such media and agents for an active substance is well known in the art.

The term "an effective amount" refers to the amount or dose of active compound(s) or a composition of the present disclosure that will lead to one or more desired effects, in particular therapeutic effects. The term can also refer to an amount of dose to maintain the uric acid level, for example, at a normal level of uric acid such as, at or below 5 mg/dL or 6 mg/dL. An effective amount or a therapeutically effective amount of a substance can vary according to factors such as the disease state, age, sex, and weight of the individual, and the ability of the substance to elicit a desired response in the individual. A dosage regimen may be adjusted to provide the optimum therapeutic response (such as sustained beneficial effects). For example, several divided doses may be administered daily or the dose may be proportionally reduced as indicated by the exigencies of the therapeutic situation.

In some embodiments, the effective amount decreases the serum levels of uric acid to achieve normal serum uric acid levels. For example, the effective amount can decrease uric acid levels by at least about 5%, 10%, 15%, 20%, 30%, 40%, 50%, 60%, 75%, 80%, 85%, 90%, 95%, or any percentage in between. In embodiments of the present disclosure, the effective amount decreases uric acid from about 5% to 50%, from 5% to 95%, from 10% to 50%, from 10% to 20%, from 10% to 30%, from 10% to 40%, from 10% to 50%, from 10% to 60%, from 10% to 70%, from 10% to 95%, from 15% to 50%, from 15% to 95%, from 20% to 40%, or from 20% to 60%. Alternatively, the effective amount can decrease serum uric acid levels by at least about 0.5 mg/dL (about 30 µM), 1 mg/dL (about 60 µM), 2 mg/dL (about 119 µM), 2.5 mg/dL (about 149 µM) or 3 mg/dL (about 178 µM). In embodiments of the present disclosure, the effective amount can decrease blood uric acid levels from about 0.5 mg/dL (about 30 µM) to 3 mg/dL (about 178 µM), from 1 mg/dL (about 60 µM) to 3 mg/dL (about 178 µM), or from 2 mg/dL (about 119 µM) to 3 mg/dL (about 178 µM).

Scyllo-inositol is a cyclohexane polyol, isomeric with myo-inositol, but differing in the orientation of the six hydroxyl groups around the ring. The structural formula of scyllo-inositol is depicted below in both 3-dimensional and planar drawings.

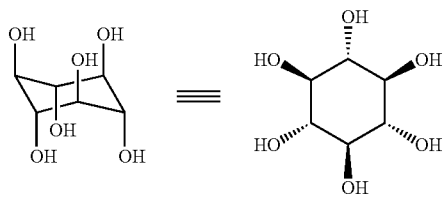

It is also known as scyllitol, quercinitol, and 1,2,3,4,5,6-cyclohexanehexyl, (1alpha,2beta,3alpha,4beta,5alpha,6beta). Scyllo-inositol is commercially available in the Sigma Aldrich catalog under CAS no. 488-59-5 or may be made by oxidation of myo-inositol to scyllo-inosose and stereospecific reduction using a metal catalyst and hydrogen following known procedures. Scyllo-inositol may alternatively be produced using process steps described by Sarmah M. and Shashidhar, M., Carbohydrate Research, 2003, 338, 999-100, Husson, C., et al, Carbohydrate Research 307 (1998) 163-165, Weissbach, A., J Org Chem (US), 1958, 23:329-330; Chung, S. K. et al., Bioorg Med. Chem. 1999, 7(11):2577-89; or Kiely D. E., and Fletcher, H. G., J. American Chemical Society (US) 1968, 90:3289-3290; and described in DE 3,405,663 (Merck patent GMBH). Scyllo-inositol may also be made according to the procedures in U.S. Patent Application Publication No. 2006/0240534 (see also WO05035774, EP1674578, JP2003102492, and JP09140388) assigned to Hokko Chemical Industries.

In some embodiments of the present disclosure, the methods, compositions, and combinations disclosed herein may comprise an analog or derivative of scyllo-inositol, for example, an analog or derivative as disclosed in International Published Applications WO 2007/041855 and WO 2007/119108.

Uric acid is denoted by the following systematic nomenclature: 7,9-dihydro-1H-purine-2,6,8(3H)-trione. Urate is the anion of uric acid and may be found physiologically as the ammonium, calcium, or sodium salt, among other possible physiological counterions. Uric acid exists along with the ionized urate form physiologically. Unless otherwise constrained by the context in which it is used, uric acid includes urate salts.

Scyllo-inositol may be administered by any of the accepted modes of systemic administration including oral, subdermal, intramuscular, parenteral, and other systemic routes of administration. Any pharmaceutically acceptable mode of administration can be used, including solid, semi-solid, or liquid dosage forms, such as for example, tablets, pills, capsules, powders, liquids, suspensions, or the like. Those dosage forms may be in a unit dosage form suitable for administration of precise dosages, as immediate or in sustained or controlled release forms, such as extended, release forms for the prolonged administration of the compound at a predetermined rate. Sustained or continuous release compositions containing scyllo-inositol are described, for example, in WO 2007/101353.

Compositions of scyllo-inositol for use in the present disclosure will typically include at least one pharmaceutically acceptable component chosen from a carrier, an excipient, and a vehicle and the active compound and, in addition, may include other medicinal agents, pharmaceutical agents, carriers, adjuvants, and the like. Carriers, excipients, and vehicles are generally selected based on the intended form of administration, and consistent with conventional pharmaceutical practices. Suitable pharmaceutical carriers, excipients, and vehicles are described in the standard text, *Remington: The Science and Practice of Pharmacy* (21st Edition, Popovich, N (eds), Advanced Concepts Institute, University of the Sciences in Philadelphia, Philadelphia, Pa. 2005).

The compositions are compounded into unit dosage forms containing a predetermined, standard amount of the active compound, to make dosing and patient compliance simpler. For example, capsules, tablets, or controlled release delivery forms may be formulated and manufactured to comprise, for example, 200 mg, 250 mg, 350 mg, 500 mg, 750 mg, 800 mg, 1000 mg, or 2000 mg of scyllo-inositol. Such tablets or controlled release delivery forms may be used for administration of one unit dosage form or any combination of unit dosage forms, that is more than one unit dosage form, to achieve a total dosage required as determined by the prescribing physician.

The amount of active compound administered will be dependent on the subject being treated, the amount or severity of the condition (e.g. hyperuricemia), the particular disease state being treated in which hyperuricemia is a cause or risk factor, the manner of administration, and the judgment of the prescribing physician. However, an effective dosage ranges from about 150 mg/day to 7000 mg/day, for example, from about 150 mg/day to about 6000 mg/day, such as from about 150 mg/day to about 4000 mg/day, such as from about 150 mg/day to about 3000 mg/day, from about 150 mg/day to about 2000 mg/day, from about 200 mg/day to about 3000 mg/day, from about 150 mg/day to about 4000 mg/day, from about 200 mg/day to about 4000 mg/day, or from about 500 mg/day to about 3000 mg/day. Daily dosages may be achieved by once a day, twice a day, three times a day, or four times daily administration. The duration of treatment can be adapted to the conditions of the patient with the aim to obtain long term normal uric acid levels.

Scyllo-inositol may be administered in combination with other medications (such as second therapeutic agents) or other medical procedures to treat the same or other aspects of the disease state being treated. A second therapeutic agent may either be within the same pharmaceutical composition (combination compositions), or the two agents may be administered in separate compositions at substantially the same time or at different times as required in the judgment of the prescribing physician. In some embodiments of the present disclosure, the second therapeutic agent can be an agent for the prophylaxis and/or treatment of hyperuricemia; gout arthritis; gouty kidney; urolithiasis; hypertension or hypertensive complications; hyperlipidemia or hyperlipidemic complications; kidney failure; cardiovascular disorder; cancer; or a cerebrovascular disorder. In a further embodiment, the second therapeutic agent can be an agent that increases uric acid levels in a subject. In at least one embodiment of the present disclosure, the second therapeutic agent is chosen from a diuretic (e.g., hydrochlorothiazide, furosemide), loop diuretics, angiotension-convertase inhibitors, angiotensin II receptor antagonists, renin angiotensin systems inhibitor (e.g. captopril, cilazapril, enalapril, fosinopril, lisinopril, quinapril, ramapril, zofenopril, candesartan cilexetil, eprosartan, irbesartan, losartan, tasosartan, telmisartan, and valsartan), CA antagonists, β-blockers, α,β-blockers, α-blockers, statins, anion exchange resins, probucol, fibrate agents, eicosapentaenoic acid preparations, thromboxane synthetase inhibitor, thromboxane receptor antagonist, alkalinizing urine agents such as citric acid preparations and sodium bicarbonate, cation exchange resins, aluminum hydroxide, alfacalcidol, ACE inhibitors, salicylate, pyrazinamide, ethambutol, NSAID (e.g., indomethacin, naproxen, fenbufen, pranoprofen, oxaprozin, colchicine, corticosteroid and the like), nicotinic acid, cyclosporine, 2-ethylamino-1,3,4-thiadiazole, antineoplastic agent, immunosuppressive agent, cytotoxic agent, anti-hypertensive agent and uric acid lowering agent.

In a further embodiment of the present disclosure, the second therapeutic agent is an agent for treatment of hyperlipidemia or hyperlipidemic complications including without limitation lovastatin, simvastatin, pravastatin, fluvastatin, atorvastatin, cerivastatin, colestimide, colestyramine, niceritrol, nicomol, fenofibrate, bezafibrate, clinofibrate, clofibrate, ethyl icosapentate and the like.

In yet another embodiment of the present disclosure, the second therapeutic agent is an agent for treatment of diabetes and diabetes complications including without limitation, insulin preparations, sulfonylureas, insulin secretagogues, sulfonamides, biguanides, a glucosidase inhibitors, insulin sensitizers, angiotensin-convertase inhibitors, aldose reductase inhibitors, antiarrhythmic drugs and the like, in particular, insulin, chlorpropamide, glibenclamide, glipizide, tolbutamide, glyclopyramide, acetohexamide, glimepiride, tolazamide, gliclazide, nateglinide, glybuzole, metformin hydrochloride, buformin hydrochloride, voglibose, acarbose, pioglitazone hydrochloride, mexiletine and the like.

In a further embodiment of the present disclosure, the second therapeutic agent is an agent for treatment of kidney failure, cardiovascular disorder, cerebrovascular disorder caused by hyperuricemia including without limitation loop diuretics (e.g., furosemide), citric acid preparations, sodium bicarbonate, cation exchange resins, aluminum hydroxide, alfacalcidol, β-blockers (e.g., propranolol hydrochloride), ACE inhibitors (e.g., captopril), cardiac stimulants (e.g., digoxin), angina pectoris therapeutic agents (e.g., isosorbide nitrate), Cα antagonists (e.g., diltiazem hydrochloride), uric acid production suppressants (e.g., allopurinol), amino acid preparations, hyperammonemia improvers, therapeutic agents for antiarrhythmia (e.g., mexiletine) and therapeutic agents for anemia (e.g., mepitiostane, erythropoietin).

The dose of the second therapeutic agent can be determined according to the dose employed clinically, and having regard to the age and body weight of the subject of administration, condition, administration time, dosage form, administration method, combination and the like. The mode of administration of the second therapeutic agent is not particularly limited.

Medical procedures which may be used in combination with scyllo-inositol include, without limitation, surgical procedures which are likely to lead to post-operative elevation in serum uric acid levels such as cardiovascular surgery, prolonged orthopedic surgeries, organ transplantation, abdominal/GI-related surgery, gynecological-related surgery, among others, and procedures such as administration of contrast agents or nephrotoxins which can increase the risk for acute renal failure.

Scyllo-inositol may be administered in substantially pure form as a powder or a powder contained in, for example, a gelatin capsule. It may also be administered in solid compositions with conventional non-toxic carriers, for example, mannitol, lactose, starch, magnesium stearate, sodium saccharin, talcum, cellulose, glucose, sucrose, magnesium carbonate, and the like. Liquid pharmaceutically administrable compositions can, for example, be prepared by dissolving, dispersing, or otherwise mixing scyllo-inositol, as defined above, and optional pharmaceutical adjuvants in a sterile carrier, such as, for example, water, saline, aqueous dextrose, glycerol, ethanol, mineral or vegetable oils and the like to thereby form a solution or suspension. If desired, the pharmaceutical composition to be administered may also contain minor amounts of non-toxic auxiliary pH buffering agents and the like, for example, sodium acetate, sorbitan monolaurate, or triethanolamine oleate. Actual methods of preparing such dosage forms are known, or will be apparent to those skilled in this art; for example, see Remington's Pharmaceutical Sciences, Mack Publishing Company, Easton, Pa., 15th Edition, 1975.

Dosage forms or compositions containing scyllo-inositol in the range of 0.25% to 100%, with the balance, when less than 100%, made up from non-toxic excipients and carriers may be prepared. For oral administration, a pharmaceutically acceptable non-toxic composition is formed, optionally with the incorporation of any of the normally employed pharmaceutical excipients, and may contain 1% to 100% active ingredient, such as from 25% to 75%. Percentages recited in the compositions in the specification and claims are weight percentages or w/w.

Parenteral administration is generally characterized by injection, whether subcutaneously or intramuscularly. Injectables can be prepared in conventional forms, either as liquid solutions or suspension, solid forms suitable for solution or suspension in liquid prior to injection, or as emulsions. Suitable excipients include, for example, water, saline, aqueous dextrose, glycerol, ethanol or the like. In addition, if desired, the pharmaceutical compositions may also contain minor amounts of non-toxic substances such as wetting or emulsifying agents, auxiliary pH buffering agents and the like, for example, sodium acetate, sorbitan monolaurate, or triethanolamine oleate.

For delayed or extended release scyllo-inositol may be included in a pharmaceutical composition formulated for slow release, such as in microcapsules formed with biocompatible polymers, polymer coated multiparticulates or in liposomal carrier systems according to methods known in the art. The compositions may also be advantageously administered as bi-layer tablets containing an immediate release component and a delayed release component.

For extended release of active agent, the scyllo-inositol may be covalently conjugated to a water soluble polymer, such as a polylactide or biodegradable hydrogel derived from an amphipathic block copolymer, as described in U.S. Pat. No. 5,320,840. The scyllo-inositol may also be incorporated into a polymer or multi-polymer matrix having properties that release the active compound through diffusion from the matrix, erosion of the matrix, or a combination of diffusion and erosion.

The present disclosure is further directed to a kit comprising a first container comprising a pharmaceutical composition comprising an amount of scyllo-inositol effective to lower a mammal's uric acid level in blood compared to a baseline level and at least one pharmaceutically acceptable component chosen from a carrier, an excipient, and a vehicle. The kit further comprises a second container comprising a second therapeutic agent. The kit can be a package which houses a container which contains a scyllo-inositol or pharmaceutical composition disclosed herein, and also houses instructions for administering the scyllo-inositol or pharmaceutical composition disclosed herein. The disclosure further relates to a commercial package comprising a scyllo-inositol or pharmaceutical composition disclosed herein together with instructions for simultaneous, separate or sequential use. A label may further include amount, frequency, and method of administration.

The present disclosure will be described in greater detail by way of specific examples. The following examples are offered for illustrative purposes and are not intended to limit the present disclosure in any manner. Those of skill in the art will readily recognize a variety of parameters which can be changed or modified to yield essentially the same results.

EXAMPLES

Example 1

A Phase 1 single site, open-label multiple dosing study evaluating a scyllo-inositol formulation was conducted in healthy adult subjects. Approximately 8 healthy male subjects received 2000 mg of scyllo-inositol twice daily (4-500 mg tablets orally administered twice a day) for 10 days. Blood samples were collected 12 hours prior to the first dose (day 0) and on days 6, 14, and 21.

Scyllo-inositol 500 mg capsules were BSE/TSE-free soft gelatin, white, opaque capsules and no excipients were used in the finished product. Capsules were supplied in 60-mL, oblong, white pharmaceutical high density polyethylene (HDPE) bottles with white caps. Each 60-mL bottle contained 30 capsules of 500 mg strength scyllo-inositol.

In all 8 subjects, uric acid decreased between Day 0 and Day 6; this decrease ranged from approximately 12 to 175 μmol/L, then returned to Day 0 values by Day 21, the last follow-up visit. Serum uric acid levels decreased in all subjects following the start of treatment, although mean uric acid levels remained within the normal range during the study. Maximal decreases were seen at Day 6, and ranged from approximately 12 to approximately 172 μmol/L between Day 0 and Day 6, and returned towards baseline by Day 21.

The mean uric acid values and change from baseline values are provided in Table 1 for all the subjects. Overall, a decrease in serum uric acid levels was observed in all subjects following scyllo-inositol administration.

TABLE 1

Summary of uric acid values in micromole per liter.

|  | Baseline | Day 6 | Day 14 | Day 21 |
| --- | --- | --- | --- | --- |
| N | 8 | 8 | 8 | 8 |
| Mean | 305.6 | 216.8 | 243.9 | 289.2 |
| SD | 38.54 | 29.94 | 22.48 | 30.48 |
| Median | 300.4 | 226.0 | 237.9 | 291.5 |
| Min, Max | 256, 375 | 155, 250 | 196, 274 | 250, 333 |
| N | — | 8 | 8 | 8 |
| Mean Change | — | −88.8 | −70.6 | −16.4 |
| SD Change | — | 51.85 | 43.06 | 44.25 |
| Median Change | — | −72.6 | −74.4 | −23.8 |
| Min, Max Change | — | −172, −12 | −131, −12 | −83, 65 |

Note:
(1) Baseline is defined as the evaluation performed on Day 0; and Change from Baseline equals value at indicated time point − value at Baseline.

Example 2

Multiple Ascending Dose Study of Orally Administered Scyllo Inositol Every Twelve Hours for Seven Days in Healthy Elderly Subjects A single-center, randomized, placebo-controlled, multiple ascending dose study evaluating a scyllo-inositol formulation was conducted in healthy elderly subjects. Approximately 32 healthy subjects (men and women) participated in one or four cohorts consisting of 8 subjects each (i.e., 6 on active drug and 2 on placebo). Subjects received drug twice daily (BID) (every 12 hours) for 7 days. The dosage levels of the scyllo-inositol were 200 mg BID (400 mg/d total), 700 mg BID (1400 mg/d total), 1500 mg BID (3000 mg/d total) and 3000 mg BID (6000 mg/d total) given every 12 hours. Blood samples were collected from each subject on days 0, 4, 7, and 12. Uric acid levels were measured in the blood samples and the results are shown in FIGS. 1 and 2.

Scyllo-inositol 200 and 500 mg capsules were bovine spongiform encephalopathy (BSE)/transmissible spongiform encephalopathy (TSE)-free soft gelatin, white, opaque capsules and no excipient was used in the finished product. Capsules were supplied in 60-mL, oblong, white pharmaceutical high density polyethylene (HDPE) bottles with white caps. Each 60-mL bottle contained 30 capsules of 200 or 500 mg scyllo-inositol.

A dose-related decrease in mean uric acid levels was observed at Days 4 and 7, which partially resolved by Day 12. The baseline mean uric acid for all subjects treated with scyllo-inositol was 297.2 µmol/L-5 mg/dL (normal range: 269.6 to 316.2 µmol/L) and for placebo subjects was 270.3 µmol/L. At Day 4, mean decreases from baseline across all scyllo-inositol treatment groups were observed: 200 mg (−7.9 µmol/L-0.1 mg/dL), 700 mg (−51.5 µmol/L-0.87 mg/dL), 1500 mg (−70.4 µmol/L-1.2 mg/dL), and 3000 mg (−83.3 µmol/L-1.4 mg/dL). A mean decrease from baseline of ±9.9 µmol/L-0.1 mg/dL was observed in the placebo group at this time point.

By Day 7, decreases from baseline continued among subjects treated with scyllo-inositol, but a dose-response effect was not as apparent: 200 mg (−25.8 µmol/L), 700 mg (−70.4 µmol/L), 1500 mg (−88.2 µmol/L), and 3000 mg (−85.3 µmol/L). At Day 7, the mean decrease from baseline in subjects treated with placebo was −24.5 µmol/L.

By Day 12, mean increases from baseline in uric acid were seen in the scyllo-inositol 200 mg group (+25.8 µmol/L) and the placebo group (+29.0 µmol/L). Mean decreases in the scyllo-inositol 700 mg, 1500 mg, and 3000 mg groups at Day 12 were −1.0, −27.8, and −29.7 µmol/L, respectively. Results are summarized at Tables 2-5.

TABLE 2

Summary of uric acid results at Baseline in micromole per liter.

|  | Placebo | 200 mg | 700 mg | 1500 mg | 3000 mg |
|---|---|---|---|---|---|
| N | 9 | 6 | 6 | 6 | 6 |
| Mean | 270.3 | 316.2 | 269.6 | 303.3 | 299.4 |
| SD | 67.43 | 108.08 | 104.02 | 76.54 | 51.81 |
| Median | 285.5 | 318.2 | 258.7 | 279.6 | 300.4 |
| Min, Max | 167, 381 | 149, 458 | 161, 410 | 220, 434 | 226, 363 |

Note:
(1) Baseline for serum chemistry is the result on Day 0; and
(2) Change From Baseline = value at indicated time point − value at Baseline.

TABLE 3

Summary of uric acid results at Day 4 in micromole per liter.

|  | Placebo | 200 mg | 700 mg | 1500 mg | 3000 mg |
|---|---|---|---|---|---|
| N | 9 | 6 | 6 | 6 | 6 |
| Mean | 260.4 | 308.3 | 218.1 | 233.0 | 216.1 |
| SD | 69.29 | 106.76 | 86.66 | 52.86 | 44.77 |
| Median | 243.9 | 330.1 | 175.5 | 237.9 | 226.0 |
| Min, Max | 161, 357 | 143, 410 | 143, 351 | 155, 291 | 161, 262 |
| N | 9 | 6 | 6 | 6 | 6 |
| Mean Change | −9.9 | −7.9 | −51.5 | −70.4 | −83.3 |
| SD Change | 30.76 | 33.58 | 36.60 | 50.11 | 20.26 |
| Median Change | −5.9 | −11.9 | −62.5 | −71.4 | −83.3 |
| Min, Max Change | −48, 24 | −48, 54 | −101, 0 | −143, 12 | −107, −59 |

Note:
(1) Baseline for serum chemistry is the result on Day 0; and
(2) Change From Baseline = value at indicated time point − value at Baseline.

TABLE 4

Summary of uric acid results at Day 7 in micromole per liter.

|  | Placebo | 200 mg | 700 mg | 1500 mg | 3000 mg |
|---|---|---|---|---|---|
| N | 9 | 6 | 6 | 6 | 6 |
| Mean | 258.7 | 290.5 | 199.3 | 215.1 | 214.1 |
| SD | 64.06 | 102.29 | 74.17 | 38.26 | 45.61 |
| Median | 229.0 | 333.1 | 169.5 | 229.0 | 214.1 |
| Min, Max | 190, 369 | 143, 387 | 125, 309 | 155, 256 | 149, 268 |
| N | 8 | 6 | 6 | 6 | 6 |
| Mean Change | −24.5 | −25.8 | −70.4 | −88.2 | −85.3 |
| SD Change | 28.87 | 41.15 | 38.81 | 61.86 | 23.39 |
| Median Change | −17.8 | −17.8 | −83.3 | −77.3 | −74.4 |
| Min, Max Change | −65, 18 | −77, 18 | −107, −12 | −196, −24 | −131, −71 |

Note:
(1) Baseline for serum chemistry is the result on Day 0; and
(2) Change From Baseline = value at indicated time point − value at Baseline.

TABLE 5

Summary of uric acid results at Day 12 in micromole per liter.

|  | Placebo | 200 mg | 700 mg | 1500 mg | 3000 mg |
|---|---|---|---|---|---|
| N | 8 | 6 | 6 | 6 | 6 |
| Mean | 312.3 | 342.0 | 268.7 | 275.6 | 269.6 |
| SD | 81.12 | 108.75 | 99.20 | 71.14 | 51.40 |
| Median | 294.4 | 368.8 | 237.9 | 279.6 | 270.6 |
| Min, Max | 214, 428 | 184, 476 | 167, 410 | 196, 399 | 208, 345 |
| N | 8 | 6 | 6 | 6 | 6 |
| Mean Change | 29.0 | 25.8 | −1.0 | −27.8 | −29.7 |
| SD Change | 49.91 | 25.14 | 28.00 | 29.06 | 37.24 |
| Median Change | 14.9 | 26.8 | 3.0 | −29.7 | −23.8 |
| Min, Max Change | −24, 101 | −12, 59 | −54, 30 | −65, 18 | −83, 18 |

Note:
(1) Baseline for serum chemistry is the result on Day 0; and
(2) Change From Baseline = value at indicated time point − value at Baseline.

The mean change from baseline to day 7 versus placebo was used to determine statistical significance. The ANCOVA model and a simple t-test resulted in $p<0.003$ for both, 95% confidence interval (CI) for mean difference (PLC-TRT) was (0.34, 1.37), with point estimate of 0.85. The ANCOVA looked at the change of uric acid levels in controls from starting levels of uric acid; the software used was SAS 9.1.3. The confidence interval did not include 0 and the 95% CI difference between treatment and placebo demonstrated statistical significance. The point estimate of 0.85 is a population parameter in dosed subjects. The simple t-test did not control for variables.

Example 3

Pharmaceutical Composition

Scyllo-inositol 250 mg and 500 mg capsules were prepared with bovine spongiform encephalopathy (BSE)/transmissible spongiform encephalopathy (TSE)-free hard gelatin, immediate release (IR) grey, opaque capsules. Talc is used as an excipient in the finished product In addition, scyllo-inositol 1000 mg IR tables were prepared comprising microcrystalline, fumed silica, magnesium stearate and a polyvinyl alcohol (PVA)-based coating.

The present disclosure and manner and process of using it, are now described in such full, clear and concise terms so as to enable a person skilled in the art to which it pertains to make and use the same. It is also to be understood that the foregoing description is of exemplary embodiments of the present disclosure and that modifications may be made hereof without departing from the scope or spirit of the present disclosure as set forth in the claims.

What is claimed is:

1. A method of decreasing uric acid levels of a patient in need thereof in one or more tissues or organs, blood, serum, urine, or combinations thereof comprising:
   administering to the patient an effective amount of scyllo-inositol to decrease the uric acid level in the patient compared to the patient's uric acid level before administration.

2. The method of claim 1, wherein the scyllo-inositol is administered in combination with a second therapeutic agent.

3. The method of claim 1, wherein the scyllo-inositol is administered in a unit dosage form.

4. The method of claim 1, wherein the amount of scyllo-inositol administered ranges from 150 mg/day to about 7000 mg/day.

5. A method of treating a patient suffering from a condition associated with aberrant levels of uric acid comprising: administering to the patient an effective amount of scyllo-inositol to decrease the uric acid level in the patient compared to the patient's uric acid level before administration, wherein the condition is chosen from gout; a recurrent gout attack, gouty tophus, gouty arthritis; gouty nephropathy; hyperuricemia; chronic hyperuricemia of myeloid metaplasia or chronic hyperuricemia of blood dyscrasia; gout-like symptoms of Lesch-Nyhan syndrome or Kelley-Seegmiller syndrome; urolithiasis; and urate lithiasis.

6. A method of treating hyperuricemia in a patient in need thereof comprising:
   administering to the patient an effective amount of scyllo-inositol to decrease the uric acid level in the patient compared to the patient's uric acid level before administration.

7. The method of claim 6, wherein the uric acid level in the blood of the patient is greater than or equal to about 360 µM, as measured in blood serum before administration.

8. The method of claim 6, wherein the patient is suffering from atheroscleropathy; arterioloscleropathy; metabolic syndrome; hypertension; cardiovascular disease; coronary heart disease; urolithiasis; or urate lithiasis.

9. The method of claim 6, wherein the amount of scyllo-inositol administered ranges from about 150 mg/day to about 7000 mg/day.

10. The method of claim 6, wherein scyllo-inositol is administered in a unit dosage form.

11. The method of claim 10, wherein the unit dosage form is chosen from an immediate release dosage form and an extended release dosage form.

12. The method of claim 10, wherein the unit dosage form comprises 150 mg, 250 mg, 500 mg, 750 mg, 800 mg, 1000 mg, or 2000 mg of scyllo-inositol.

13. A method of treating gout in a patient in need thereof comprising:
   administering to the patient an effective amount of scyllo-inositol to decrease the uric acid level in the patient compared to the patient's uric acid level before administration.

14. The method of claim 13, wherein the amount of scyllo-inositol administered ranges from about 150 mg/day to about 7000 mg/day.

15. The method of claim 13, wherein scyllo-inositol is administered in a unit dosage form.

16. The method of claim 15, wherein the unit dosage form is chosen from an immediate release dosage form and an extended release dosage form.

17. The method of claim 15, wherein the unit dosage form comprises 150 mg, 250 mg, 500 mg, 750 mg, 800 mg, 1000 mg, or 2000 mg of scyllo-inositol.

18. A method of treating hyperuricemia in a patient in need thereof comprising:
   administering to the patient an effective amount of a pharmaceutically acceptable unit dosage form comprising scyllo-inositol to decrease the uric acid level in the patient compared to the patient's uric acid level before administration.

19. A method of treating gout in a patient in need thereof comprising:
   administering to the patient an effective amount of a pharmaceutically acceptable unit dosage form comprising scyllo-inositol to decrease the uric acid level in the patient compared to the patient's uric acid level before administration.

* * * * *

UNITED STATES PATENT AND TRADEMARK OFFICE
CERTIFICATE OF CORRECTION

| | | |
|---|---|---|
| PATENT NO. | : 8,748,496 B2 | Page 1 of 1 |
| APPLICATION NO. | : 12/560113 | |
| DATED | : June 10, 2014 | |
| INVENTOR(S) | : Jesse M. Cedarbaum | |

It is certified that error appears in the above-identified patent and that said Letters Patent is hereby corrected as shown below:

TITLE PAGE:

Item (73) reads:

Assignee: Elan Pharmaceuticals, Inc., South San Francisco, CA (US)

Should read:

Assignee: Transition Therapeutics Ireland Limited, Dublin, Ireland

Signed and Sealed this
Thirtieth Day of September, 2014

Michelle K. Lee
*Deputy Director of the United States Patent and Trademark Office*